(12) United States Patent
Ruegg et al.

(10) Patent No.: US 9,290,768 B2
(45) Date of Patent: Mar. 22, 2016

(54) ENGINEERED MICROORGANISMS HAVING RESISTANCE TO IONIC LIQUIDS

(71) Applicant: Lawrence Livermore National Security, LLC, Livermore, CA (US)

(72) Inventors: Thomas Lawrence Ruegg, Berkeley, CA (US); Michael P. Thelen, Danville, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 232 days.

(21) Appl. No.: 13/935,325

(22) Filed: Jul. 3, 2013

(65) Prior Publication Data

US 2014/0038848 A1 Feb. 6, 2014

Related U.S. Application Data

(60) Provisional application No. 61/667,873, filed on Jul. 3, 2012.

(51) Int. Cl.
*C12P 1/00* (2006.01)
*C12P 7/10* (2006.01)
*C12N 15/70* (2006.01)
*C07K 14/265* (2006.01)
*C12N 1/22* (2006.01)

(52) U.S. Cl.
CPC .............. *C12N 15/70* (2013.01); *C07K 14/265* (2013.01); *C12N 1/22* (2013.01); *C12P 7/10* (2013.01); *Y02E 50/16* (2013.01)

(58) Field of Classification Search
None
See application file for complete search history.

(56) References Cited

PUBLICATIONS

Deangelis et al, "Complete genome sequence of *"Enterobacter lignolyticus"* SCF1", *Standard in Genomic Science*, 5:69-85 (2011).
Khudyakov et al., "Global transcriptome response to ionic liquid by a tropical rain forest soil bacterium, *Enterobacter lignolyticus*", *PNAS*, E2173-E2182 (2012).
Ogawa et al., "KmrA Multidrug Efflux Pump from *Klebiella pneumonia*", *Biol. Pharm. Bull*, 29(3): 550-553 (2006).

*Primary Examiner* — David J Steadman
*Assistant Examiner* — Paul Holland
(74) *Attorney, Agent, or Firm* — Kilpatrick Townsend & Stockton LLP

(57) ABSTRACT

The present invention provides for a method of genetically modifying microorganisms to enhance resistance to ionic liquids, host cells genetically modified in accordance with the methods, and methods of using the host cells in a reaction comprising biomass that has been pretreated with ionic liquids.

11 Claims, 8 Drawing Sheets

Figure 1

```
Methyl viologen resistance protein smvA
OS=Klebsiella oxytoca 10-5246
GN=HMPREF9690_02145 PE=4 SV=1
• Length = 496
• Score = 734 bits (1894)
• Expect = 0.0
• Identities = 383/491 (78%)
• Positives = 434/491 (88%)

Query:   1   MFRQWVTLFAILLVYIPVAIDATVLHVAAPTLSVSLGTSSNELLWIIDIYSLVMAGMVLP  60
             M RQW+TL AILLVY+PVAIDATVLHVAAPTLS+SLGTSSNELLWIIDIYSLVMAGMVLP
Sbjct:   1   MSRQWLTLVAILLVYLPVAIDATVLHVAAPTLSMSLGTSSNELLWIIDIYSLVMAGMVLP  60

Query:  61   MGALGDRIGFKRLLLSGSGLFGLASLAAAFAPSAMWLIAARACLAVGAAMIVPATLAGIR  120
             MGALGD+IGFKRLLL GS +FG++SLAAAF+P+A+ LIA+RA LA+GAAMIVPATLAGIR
Sbjct:  61   MGALGDKIGFKRLLLLGSAIFGVSSLAAAFSPTALALIASRALLAIGAAMIVPATLAGIR  120

Query: 121   NTFSEARHRNMALGLWATIGSGGAAFGPLIGGIVLEHFWWGAVFLINVPIVLVVMAVSAR  180
             NTFS+ARHRNMALGLWA IGSGGAAFGPL+GGI+LEHF+WG+VFLINVPIVL V+A SAR
Sbjct: 121   NTFSQARHRNMALGLWAAIGSGGAAFGPLVGGILLEHFYWGSVFLINVPIVLAVIAFSAR  180

Query: 181   VVPWQPGRREQPLNFTHAVMLVAAILLLVWSAKSAIKGSEGLGFVALALLVGGVLLTAFV  240
             +VP QP RREQPLN T A+ML+ AIL+LV+SAKSA+KG    L    LVG  LL  FV
Sbjct: 181   MVPRQPARREQPLNLTQALMLIVAILMLVFSAKSALKGQMALWLTGSIALVGLALLVRFV  240

Query: 241   RIQLAARTPMIDMRLFTHRIILCGVMMAITALATLVGFELLMAQELQFVHGKTPFEAGLF  300
             R QL+A TPM+DMRLFTHRIIL GVMMA+TAL TLVGFELLMAQELQFVHGKTPFEAGLF
Sbjct: 241   RQQLSAATPMVDMRLFTHRIILSGVMMAMTALITLVGFELLMAQELQFVHGKTPFEAGLF  300

Query: 301   MLPVMLASGFSGPIAGILVSRIGLREVATGGMMLSALSFLGLSMTDFTTQQWQAWGLMTM  360
             MLP+MLASGFSGP+AG++VSR+GLR VATGGM+LSALSFLGLSMTDF++QQW AWGLM +
Sbjct: 301   MLPLMLASGFSGPVAGVMVSRLGLRLVATGGMLLSALSFLGLSMTDFSSQQWLAWGLMIL  360

Query: 361   LGFSAASALLASTAAIMAAAPKEKAAAAGAIETMAYELGAGLGIAVFGLILTRSYSGSIL  420
             LGFS ASALLAS +AIMAAAPKEKAAAAGAIETMAYELGAGLGIA+FGLILTRSYS SI+
Sbjct: 361   LGFSVASALLASGSAIMAAAPKEKAAAAGAIETMAYELGAGLGIALFGLILTRSYSSSIV  420

Query: 421   LPDGLLAGEAARASSSIGEAVQLAQTLEQPQAMAVIDAAKTAFISSHSVVLFSAGGMLLA  480
             LP G+    AA+ASSSI EA+ LAQ+L   A ++I AAKTAFIS+HS+VL +AG +LL
Sbjct: 421   LPAGVDGQAAAQASSSISEAIALAQSLPAVPAHSLIAAAKTAFISAHSIVLATAGVLLLL  480

Query: 481   LAVGVWFGLAK  491
             LA G+W  LA+
Sbjct: 481   LAAGIWRSLAQ  491
```

ENGINEERED MICROORGANISMS HAVING RESISTANCE TO IONIC LIQUIDS

CROSS-REFERENCE TO RELATED APPLICATIONS

This application claims priority to U.S. provisional application No. 61/667,873, filed Jul. 3, 2012, which is herein incorporated by reference for all purposes.

STATEMENT AS TO RIGHTS TO INVENTIONS MADE UNDER FEDERALLY SPONSORED RESEARCH AND DEVELOPMENT

The invention was made with government support under Contract No. DE-AC02-05CH11231 awarded by the U.S. Department of Energy. The government has certain rights in the invention.

REFERENCE TO A SEQUENCE LISTING SUBMITTED AS AN ASCII TEXT FILE

The Sequence Listing written in file-108-1.txt, created on Aug. 13, 2013, 24,576 bytes, machine format IBM-PC, MS-Windows operating system, is hereby incorporated by reference.

BACKGROUND OF THE INVENTION

Biomass feedstock pretreatment with ionic liquids (ILs) reduces recalcitrance of lignocellulose to degradation. However, ILs are often toxic to microorganisms used subsequently for saccharification and fermentation and the low levels of IL that can remain after pretreatment inhibit the growth of the microorganism used in saccharification and/or fermentation reactions. There is therefore a need to improve IL tolerance of such organisms. This invention addresses this need.

SUMMARY OF THE INVENTION

In one aspect, this invention relates to a method of increasing tolerance of a microorganism, e.g., *E. coli*, to ILs. The method comprises engineering the microorganism to express a gene encoding a Major Facilitator Superfamily (MFS1) protein. The invention further provides recombinant microorganisms engineered to express a MFS1 protein and methods employing such microorganisms to process biomass.

In one aspect, the invention provides a recombinant microorganism having resistance to ionic liquids, e.g., an ionic liquid where the anion is Cl⁻ or acetate, wherein the microorganism comprises a heterologous gene encoding a MFS1 polypeptide, wherein the MFS1 polypeptide has at least 70% identity, or at least 75%, 80%, or 85% identity, to SEQ ID NO:2. In some embodiments, the MFS1 polypeptide has at least 90% identity, or at least 95% identity, to SEQ ID NO:2. In some embodiments, the polypeptide comprises SEQ ID NO:2. In some embodiments, the heterologous gene is operably linked to a tet repressor sequence. In some embodiments, the microorganism is also genetically modified to express a tet repressor protein that binds to the tet repressor sequence. In some embodiments, the microorganism is a yeast or filamentous fungi. In some embodiments, the heterologous gene encoding the MFS1 polypeptide is integrated into the genome of the microorganism. In some embodiments, the heterologous gene encoding the MFS1 polypeptide is present on an extrachromosomal autonomously replicating sequence present in the microorganism.

In a further aspect, the invention provides a method of modifying a microorganism to have resistance to ionic liquids, e.g., ionic liquids where the anion is Cl⁻ or acetate, the method comprising introducing an expression cassette into the microorganism, wherein the expression cassette comprises a gene encoding a MFS1 polypeptide that has at least 70% identity, or at least 75%, 80%, or 85% identity, to SEQ ID NO:2. In some embodiments, the MFS1 polypeptide has at least 90% identity, or at least 95% identity, to SEQ ID NO:2. In other embodiments the polypeptide comprises SEQ ID NO:2. In some embodiments, the heterologous gene is operably linked to a tet repressor sequence. In some embodiments, the method further comprises engineering the microorganism to express a tet repressor that binds to the tet repressor sequence. In some embodiments, the method comprises engineering bacteria, such as *Escherichia coli* to express the MFS1 polypeptide. In other embodiments, the method comprises engineering a yeast or filamentous fungi strain to express the MFS1 polypeptide. In some embodiments, the method comprises integrating the heterologous gene encoding the MFS1 polypeptide into the genome of the microorganism.

In a further aspect, the invention provides a composition comprising a microorganism of the invention comprising a heterologous MFS1 gene that is capable of expressing MFS1. In some embodiments, the composition is a reaction mixture that comprises an ionic liquid and the microorganism of the invention. In some embodiments, the reaction mixture further comprises biomass.

In an additional aspect, the invention provides a method of increasing the yield of soluble sugar from a biomass, the method comprising incubating biomass pretreated with a microorganism genetically modified to comprise a heterologous MFS1 gene in an enzymatic hydrolysis reaction. The invention additionally provides a method of increasing the yield from a reaction in which soluble sugars are a source of carbon, e.g., a fermentation reaction that produces a biofuel, such as an alcohol, the method comprising incubating biomass pretreated with ionic liquid with a microorganism of the invention in a reaction.

In a further aspect, the invention provides a method of identifying a gene that confers tolerance to an ionic liquid to an organism, the method comprising: culturing a recombinant genomic expression library that comprises the genome of at least one microorganism that is resistant to ionic liquids under condition in a culture medium that comprises at least 0.1% ionic liquid in which genomic inserts from the genome of the microorganism are expressed; and selecting at least one colony that grow faster in the presence of at least 0.1% ionic liquid in comparison to a control that does not comprises genomic sequences from the at least one microorganism.

BRIEF DESCRIPTION OF THE DRAWINGS

FIG. 1 provides an alignment of an MFS1 protein from *Enterobacter lignolyticus* strain SCF1 (SEQ ID NO:3) with methyl viologen resistance protein smvA from *Klebsiella oxytoca* (SEQ ID NO:4). Consensus peptides=SEQ ID NOS: 5-29.

FIG. 2 shows clones from the selection protocol that were resistant to [C₂mim]Cl. All of the clones contained a common region of 2.6 kbp that includes only one complete gene sequence encoding MFS1, a member of the Major Facilitator Superfamily of Proteins.

DETAILED DESCRIPTION OF THE INVENTION

Definitions

Figure 2:
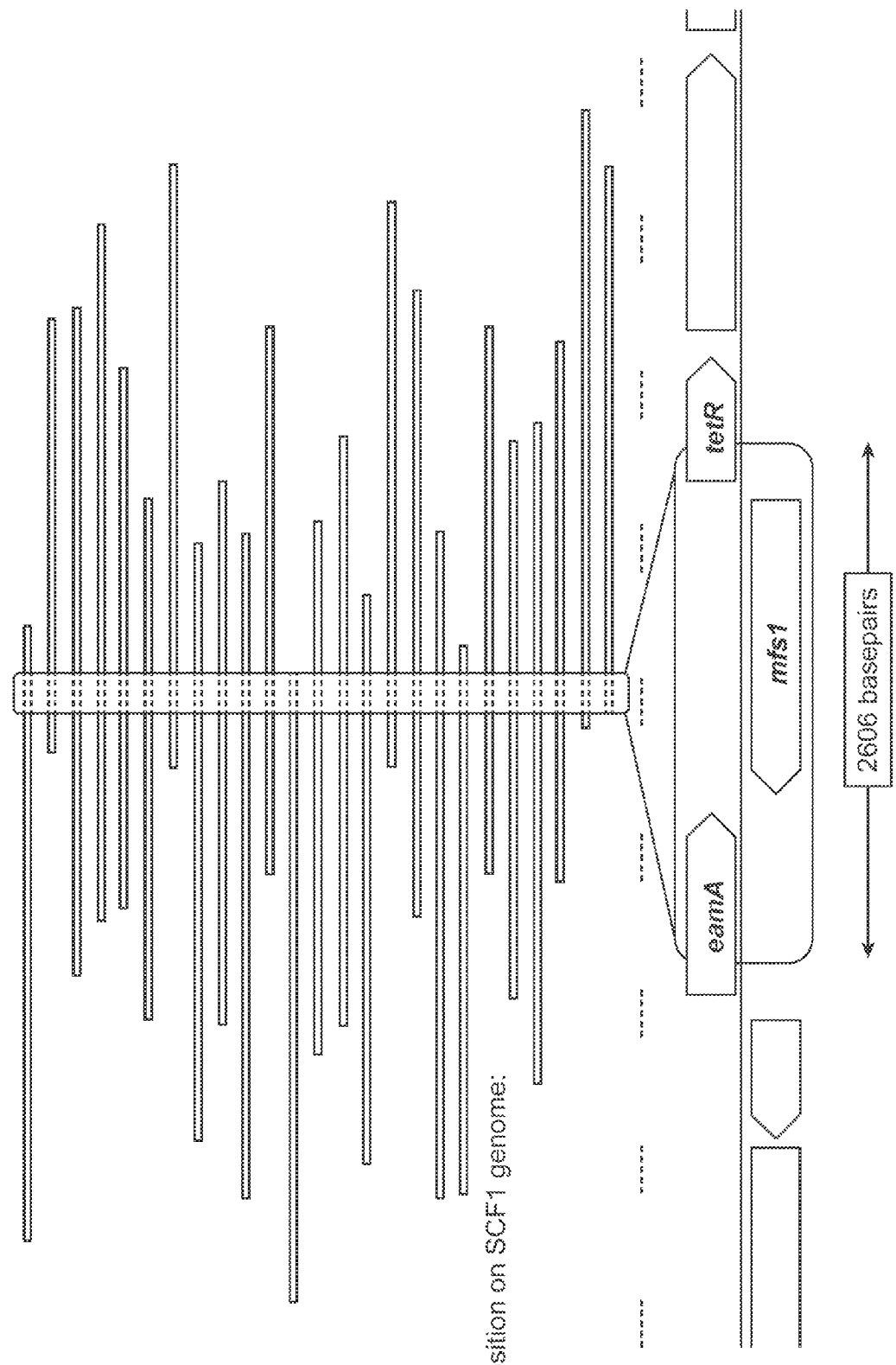
FIG. 2 provides a summary of an analysis showing that a single *Enterobacter* gene conferred IL tolerance to *E. coli*.

As used herein, the term "Major Facilitator Superfamily protein" or "MFS1 protein" are used interchangeably to refer to a membrane protein that functions as a transporter of small molecules. The term encompasses variants and interspecies homologs of the specific polypeptides described herein. A nucleic acid that encodes a MFS1 protein refers to a gene, cDNA, pre-mRNA, mRNA, and the like, including nucleic acids encoding variants and interspecies homologs of the particular amino acid sequences described herein. Thus, in some embodiments, MFS1 gene encodes a polypeptide having an amino acid sequence that has at least 40% amino acid sequence identity, or at least 45%, 50%, 55%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 300 or more amino acids, or over the length of the entire polypeptide, to an amino acid sequence of SEQ ID NO:2. SEQ ID NO:2 provides an illustrative amino acid sequence of a MFS1 proteins suitable for use in the invention.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 40%, 45%, or 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, a polynucleotide encoding a MFS1 polypeptide may have a sequence that is at least 50%, 55%, 60%, 65%, 70%, 75%, 80%, 85%, 90%, 91%, 92%, 93%, 94%, 95%, 96%, 97%, 98%, or 99% identical to SEQ ID NO:2.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. The following six groups each contain amino acids that are illustrative conservative substitutions for one another. 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety)

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a MFS1 protein operably linked to a promoter, e.g., its native promoter, where the expression cassette is introduced into a heterologous microorganism. In some embodiments, an expression cassette comprises a polynucleotide sequence encoding a MFS1 protein that is targeted to a position in the genome of a microorganism such that expression of the polynucleotide sequence is driven by a promoter that is present in the microorganism.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used herein and in the appended claims, the singular "a", "an" and "the" include the plural reference unless the context clearly dictates otherwise. Thus, for example, reference to a "host cell" includes a plurality of such host cells.

I. Introduction

Ionic liquids are used to pretreat biomass to improve the yield of soluble sugars from downstream reactions such as enzymatic hydrolysis. The invention provides methods of genetically modifying microorganisms, e.g., bacteria such as *E. coli*, to have resistance to ionic liquids.

A microorganism is typically genetically modified to express a heterologous MFS1 protein by introducing an expression cassette that comprises a polynucleotide encoding an MFS1 protein operably linked to a promoter into a microbial host cell. In some embodiments, the promoter is a constitutive promoter. In some embodiments, the promoter comprises a repressor binding site for a repressor, e.g., a tet repressor, that dissociates from the binding site when ionic liquids are present in the media in which the host cell is growing.

A microorganism modified as described herein is used in reactions that employ ionic liquids, for example, reactions comprising biomass pretreated with ionic liquids. A genetically modified microorganism as described herein provides for increased yields of soluble sugars from IL-pretreated biomass in comparison to a microorganism that has not been genetically modified to express a heterologous MFS1 protein.

Further, a microorganism modified to express MFS1 can also provide a growth advantage over a contaminating microorganism that may be present in a reaction, such as a fermentation reaction.

Genetically modified microorganisms engineered to express MFS1 can also be used for any other reactions in which it is desirable to use a microorganism that is tolerant to ionic liquids. For example, such an organism can be used in pharmaceutical reactions or other reactions where ionic liquids are used as replacement for organic solvents.

MFS1 Nucleic Acid Sequences

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009, supplements through 2012).

MFS1 nucleic acid and polypeptide sequences suitable for use in the invention include MFS1 nucleic acid sequences that encode a MFS1 polypeptide as illustrated in SEQ ID NO:2, or a substantially identical variants. Such a variant typically has at least 60%, often at least 70%, or at least 75%, 80%, 85%, or 90% identity to SEQ ID NO:2.

Various regions of MFS1 protein are defined. For example, the MFS1 polypeptide of SEQ ID NO:2 has 14 transmembrane domains. The helical regions of these domains are present an amino acids 7-29, 44-66, 73-92, 97-119, 132-154, 159-181, 193-212, 222-240, 261-283, 298-320, 327-344, 354-376, 389-411, and 468-490. A related bacterial protein from *Klebsiella oxytoca* (a methyl viologen resistance protein smvA) has 78% identity to SEQ ID NO:2. An alignment of the two proteins is shown in FIG. 1. One of skill can obtain or identify a MFS1 variant for use in the invention by using the sequence alignments to identify residues within the conserved sequences that would be expected to retain function as well as residues outside of the conserved regions that would be tolerant to substitution.

In some embodiments, an MFS1 polypeptide may be modified to have a signal sequence. For example, in some embodiments, it may be desirable to employ a signal sequence from the host cell into which the MFS1 gene will be introduced.

MFS1 activity for conferring resistance to an IL can be assessed using any number of assays. For example, a gene encoding an MFS1 protein can be introduced into a microorganism, such as bacteria, e.g., *E. coli*, and tested for the ability to grow in the presence of an IL. In the present invention, a microorganism that is resistant to an ionic liquid has improved growth in the presence of the ionic liquid when compared to the same microorganism, i.e., the same genetic background, that has not been modified to express the MFS1 polypeptide. In typical embodiments, growth in the presence of the ionic liquid, e.g., [$C_2$mim]Cl, is increased by at least 10%, 20%, 30%, 40%, or 50% or more compared the control, unmodified organism. In some embodiments, the amount of ionic liquid employed in testing is in the range of from about 1% to about to about 20% IL, e.g., about 1%, 2%, 3%, 4%, 5%, 6%, 7%, 8%, 9%, 10%, or 15% or 20%, added to the culture medium. In some embodiments, the amount of ionic liquid employed in testing is at least about 0.1% added to the culture medium. In some embodiments, the ionic liquid is [$C_2$mim]Cl. In the context of this invention, a microorganism modified to express a heterologous MFS1 polypeptide is generally resistant to at least 2% ionic liquid, and in some embodiments, is resistant to at least 10% or 20% ionic liquid, e.g., is resistant to at least 20% [$C_2$mim]Cl. In some embodiments, a microorganism modified to express a heterologous MFS1 polypeptide is resistant to at least 0.1% ionic liquid.

Isolation or generation of MFS1 polynucleotide sequences can be accomplished by any number of techniques well known in the art. In some embodiments, oligonucleotide probes based on the sequences disclosed herein can be used to identify the desired polynucleotide in a cDNA or genomic DNA library from a desired bacterial species. Probes may be used to hybridize with genomic DNA or cDNA sequences to isolate homologous genes in the same or different bacterial species.

Alternatively, the nucleic acids of interest can be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying a MFS1 gene from bacterial cells such as *Enterobacter* cells, can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990).

MFS1 nucleic acid sequences for use in the invention includes genes and gene products identified and characterized by techniques such as hybridization and/or sequence analysis using exemplary nucleic acid sequences, e.g., SEQ ID NO:1.

MFS1-encoding nucleic acid sequences may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See, e.g., See e.g., Henaut and Danchin in "*Escherichia coli* and *Salmonella*," Neidhardt, et al. Eds., ASM Pres, Washington D.C. (1996), pp. 2047-2066; Nucleic Acids Res. 20:2111-2118; Nakamura et al., 2000, Nucl. Acids Res. 28:292.

Preparation of Recombinant Vectors

To use isolated sequences in the above techniques, recombinant DNA vectors suitable for transformation of host cells are prepared. Preparation of recombinant vectors is well known in the art. For example, a DNA sequence encoding a MFS1 polypeptide can be combined with transcriptional and other regulatory sequences which will direct the transcription of the sequence from the gene in the intended cells. In some embodiments, an expression vector that comprises an expression cassette that comprises the MFS1 gene further comprises a promoter operably linked to the MFS1 gene. Such a promoter can be an MFS1 promoter from the native MFS1 gene or a heterologous promoter. In other embodiments, a promoter and/or other regulatory elements that direct transcription of the MFS1 gene are endogenous to the microorganism and an expression cassette comprising the MFS1 gene is introduced, e.g., by homologous recombination, such that the heterologous MFS1 gene is operably linked to an endogenous promoter and is expression driven by the endogenous promoter.

Expression of the MFS1 gene can be controlled by a number of regulatory sequences including promoters, which may be either constitutive or inducible; and, optionally, repressor sequences. Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. In some embodiments, an MFS1 gene is operably linked to a nucleotide sequence comprising a tet repressor binding site. An example of a tet repressor binding site is provided in the underlined region of SEQ ID NO:1.

Additional examples of regulatory regions that can be used to regulate expression of a MFS1 gene under a desired environmental conditions include lactose promoters (Lac repressor protein changes conformation when contacted with lactose, thereby preventing the Lac repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) Proc. Natl. Acad. ScL USA, 80:21-25.) As will be appreciated by those of ordinary skill in the art, these and other expression vectors may be used in the present invention, and the invention is not limited in this respect.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xy1A and xy1B genes, and prokaryotic beta-lactamase gene (VIIIa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from the gene encoding neutral alpha-amylase in *Aspergillus niger* In which the untranslated leader has been replaced by an untranslated leader from the gene encoding triose phosphate isomerase in *Aspergillus nidulans*); and mutant, truncated, and hybrid promoters thereof.

Suitable promoters of use in a yeast host cell include promoters obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

An expression vector may also comprise additional sequences that influence expression of an MFS1 gene. Such sequences include enhancer sequences or other sequences such as transcription termination sequences, and the like.

A vector expressing a MFS1 gene in accordance with the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated.

An expression vector of the invention preferably contains one or more selectable markers which permit easy selection of transformed hosts. For example, an expression vector my comprise a gene that confers antibiotic resistance (e.g., ampicillin, kanamycin, chloramphenicol or tetracycline resistance) to the recombinant host organism, e.g., a bacterial cell such as *E. coli*, that comprises the vector.

Suitable markers for other microbial host cells, such as yeast host cell are also well known and include, for example, ADE2, HIS3, LEU2, LYS2, MET3, TRP1, and URA3. Selectable markers for use in a filamentous fungal host include, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Markers for use in *Aspergillus* include the amdS and pyrG genes of *Aspergillus nidulans* ox *Aspergillus oryzae* and the bar gene of *Streptomyces hygroscopicus*. Markers for use in *Trichoderma* include bar and amdS.

An expression vector may additionally contain an element(s) that permits integration of the vector into the host's genome. In some embodiments, the expression vector may contain an element that permits autonomous replication of the vector in the cell independent of the genome.

Although any suitable expression vector may be used to incorporate the desired sequences, readily available bacterial expression vectors include, without limitation: plasmids, such as pSClOl, pBR322, pBBR1MCS-3, pUR, pEX, pMR-lOO, pCR4, pBAD24, pUC19; bacteriophages, such as Ml 3 phage and λ, phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

Expression vectors of the invention may be introduced into the host cell using any number of well-known methods, including calcium phosphate transfection, DEAE-Dextran mediated transfection, electroporation, via lipid complexes, or other common techniques.

Host Cells

Any number of microorganism can be transformed with an expression vector comprising a gene encoding a MFS1 protein in accordance with the invention. In some embodiments, the host cell is prokaryotic, such bacterial host cells. Examples of bacterial host cells include, without limitation, species assigned to the *Escherichia, Enterobacter, Azotobacter, Erwinia, Bacillus, Clostridium, Enterococcus, Lactobacillus, Lactococcu, Oceanobaciilus, Pseudomonas, Klebsiella, Proteus, Salmonella, Serratia, Shigella, Staphococcus, Strpeotcoccus, Streptomyces, Rhizobia, Vitreoscilla, Synechococcus, Synechocystis,* and *Paracoccus* taxonomical classes. In some embodiments, the prokaryotic host cells are *E. coli, Bacillus* sp. such as *Bacillus subtilis.* In some embodiments, the host cells are cyanobacteria.

In some embodiments, the host cell is a yeast. Examples of yeast host cells include *Candida, Hansenula, Kluyveromyces, Pichia, Saccharomyces, Schizosaccharomyces,* or *Yarrowia* host cells. In some embodiments, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In some embodiments, the yeast host cell is a *Kluyveromyces lactis* cell. In another embodiment, the yeast host cell is a *Yarrowia lipolytica* cell.

In other embodiments, the host cell is a filamentous fungal cell. In some embodiments, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Malbranchea, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell. For example, a filamentous fungal host cell may be an *Aspergillus awamori, Aspergillus fumigatus, Aspergillus foetidus, Aspergillus japonicus, Aspergillus nidulans, Aspergillus niger* or *Aspergillus oryzae* cell. In other embodiments, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In further embodiments, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Malbranchea cinnamomea, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell. In some embodiments, the filamentous fungal host cell is *Ustilago maydis.*

The host cells of the present invention may be genetically modified in that recombinant nucleic acids have been introduced into the host cells, and as such the genetically modified host cells do not occur in nature. The suitable host cell is one capable of expressing one or more nucleic acid constructs encoding one or more proteins for different functions.

In some embodiments, the host cell may be modified to express a tet repressor. The TetR family of transcription repressors is well known and various TetR sequences are available that can be employed to modify a host cell (see, e.g., Microbiol Mol Biol Rev. 69:326-356, 2005, which is incorporated by reference).

In some embodiments, the host cell naturally produces any of the proteins encoded by the polynucleotides of the invention. The genes encoding the desired proteins may be heterologous to the host cell or these genes may be endogenous to the host cell but are operatively linked to heterologous promoters and/or control regions which result in the higher expression of the gene(s) in the host cell. In other embodiments, the host cell does not naturally produce the desired proteins, and comprises heterologous nucleic acid constructs capable of expressing one or more genes necessary for producing those molecules.

Methods of Using Microorganism Engineered to Express MFS1

The organisms modified in accordance with the invention can be used in saccharfication or fermentation reactions that employ IL-pretreated biomass. Biomass that is pretreated with an IL include, but is not limited to, a cellulose biomass, a hemicellulose biomass, a lignocellulose biomass and mixtures thereof. In some embodiments, the biomass pretreated with an IL is a lignocellulose biomass. The biomass may be pretreated using known processes (see, for example, Hermanutz, et al., *Macromol. Symp.* 262:23-27, 2008; PCT application PCT/US2012/042790).

Examples of ILs suitable for pretreatment of the biomass and for the hydrolysis of cellulose by cellulases include, but are not limited to 1-ethyl-3-methylimidazolium acetate (EMIM Acetate), 1-ethyl-3-methylimidazolium chloride (EMIM Cl or ([C$_2$mim]Cl), 1-ethyl-3-methylimidazolium hydrogensulfate (EMIM HOSO$_3$), 1-ethyl-3-methylimidazolium methylsulfate (EMIM MeOSO$_3$), 1-ethyl-3-methylimidazolium ethylsulfate (EMIM EtOSO$_3$), 1-ethyl-3-methylimidazolium methanesulfonate (EMIM MeSO$_3$), 1-ethyl-3-methylimidazolium tetrachloroaluminate (EMIM AICI4), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AICI4), 1-butyl-3-methylimidazolium thiocyanate (BMIM SCN), 1-ethyl-2,3-dimethylimidazolium ethylsulfate (EDIM EtOSO$_3$), Tris(2-hydroxyethyl)methylammonium methylsulfate (MTEOA MeOSO$_3$), 1-methylimidazolium chloride (MIM Cl), 1-methylimidazolium hydrogensulfate (MIM HOSO$_3$), 1,2,4-trimethylpyrazolium methylsulfate, tributylmethylammonium methylsulfate, choline acetate, choline salicylate, and the like. The ionic liquid can comprises one or a mixture of the compounds. In some embodiments, the ionic liquid has an imidazolium cation. Additional suitable ILs are taught in U.S. Pat. No. 6,177,575. It will be appreciated by those of skill in the art that others ILs that will be useful in the process of the present invention are currently being developed or will be developed in the future, and the present invention contemplates their future use.

The pretreated biomass, e.g., the lignocellulose biomass, can be hydrolyzed enzymatically to break down, for example, hemicellulose and/or cellulose, into sugars. Typically, the pretreated biomass is subjected to the action of one, or several or all enzyme activities selected from a cellulase, a cellobiohydrolase, an endoglucanase, a glucano-hydrolase, a protease, a pectinase, a xylanase, a lyase, a ferulic acid esterase, and a mannanase. In one embodiment, the pretreated biomass is subjected to the action of a cellulase, such as a thermostable cellulase. Cellulases suitable for use in the present invention are commercially available from, for example, Genencor (USA) and Novozymes (Europe). For instance, Novozyme has a number of different enzymes and enzyme complexes that are specifically designed to be useful for the hydrolysis of lignocellulosic materials. Examples include, but are not limited to, the following: NS50013, which is a cellulase; NS50010, which is a beta-glucosidase; NS22086, which is a cellulase complex; NS22086, which is a xylanase; NS22118, which is β-glucosidase; NS22119, which is an enzyme complex of carbohydrates, including arabinase, β-glucanase, cellulase, hemicellulase, pectinase, and xylanase; NS22002, which is a mixture of β-glucanase and xylanase; and NS22035, which is a glucoamylase. In addition, suitable thermostable cellulases are disclosed in PCT International Publication No. WO 2010/124266, the teachings of which are incorporated herein by reference. Other hydrolases suitable for hydrolyzing the pretreated biomass, i.e., the lignocellulosic material, will be known to those of skill in the art.

Hydrolysis may additionally be carried out by contacting the pretreated biomass with a microorganism genetically modified to express an MFS1 protein in accordance with the invention. Such an organism may be additionally modified to express one or more cellulases, or other enzymes involved in lignocellulose degradation.

A host cell engineered to express MFS1 may also be genetically modified to enhance other desired properties, such as improving growth, or modified to enhance yield of a desired product in a reaction that contains ionic liquids.

A host cell modified to express MFS1 may be used in any reaction for which it is desired to employ an organism that is tolerant to ionic liquids. For example, such a host cell can be used for producing any fermentation product or other product for which sugars obtained from hydrolysis of an ionic-liquid pretreated biomass can serve as a carbon source. Examples of products include, but are not limited to, alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., H$_2$ and CO$_2$); antibiotics (e.g., penicillin and tetracycline); vitamins (e.g., riboflavin, B12, beta-carotene), fatty acids and fatty acid derivatives (as described, e.g., in PCT/US2008/068833); isoprenyl alkanoates (as described, e.g., PCT/US2008/068756, methyl butenol (as described, e.g., in PCT/US2008/068831; fatty acid esters (as described, e.g., in PCT/US2010/033299), isoprenoid-based alternative diesel fuels (as described, e.g., in PCT/US2011/059784; a polyketide synthesized by a polyketide synthase, such as a diacid (see, e.g., PCT/US2011/061900), biofuels (see, e.g., PCT/US2009/042132) and alpha-olefins (see, e.g., PCT/US2011/053787). Both the enzymatic hydrolysis and subsequent steps to produce a desired organic compound can be carried out using procedures known to and used by those of skill in the art.

Methods of Identifying Genes that Confer Resistance to Ionic Liquids

In a further aspect, the invention provides a method of screening for genes that confer resistance to ionic liquids. The method comprises preparing a genomic library comprising the genome of a microorganism resistant to ionic liquids, e.g., *Enterobacter lignolyticus* SCF1 in a vector, e.g., a vector that accommodates large inserts, e.g., at least 30 kb, and introducing the library into the desired host cells. Typically, a low copy number vector is employed to enhance stability of the library. In some embodiments, the vector is a fosmid vector or bacterial artificial chromosome that contains an f-factor origin replication. These are derived from *E. coli* f-factor which is able to stably integrate large segments of genomic DNA. When integrated with DNA from a mixed uncultured environmental sample, this makes it possible to achieve large genomic fragments in the form of a stable library. The vector may contain additional sequences such as selectable markers. The library can then be screened for colonies that are resistant to ionic liquids by plating the library onto media containing an ionic liquid of interest, e.g., [C$_2$mim]Cl, at a desired concentration, e.g., from about 1% to about 6%. Colonies that exhibit relatively fast growth can then be selected and evaluated to determine gene(s) present in the clone and further tested to determine whether the gene can confer resistance to an ionic liquid to host cells transformed with an expression vector that expresses the gene. In some embodiments, the copy number may be amplified to facilitate isolated the DNA of interest.

In some embodiments, the library comprises genomic inserts from more than one microorganism. For example, genomic DNA can be isolated from an environmental sample and a library can be screened as described above. The identity of the microorganisms from which the genomic DNA is isolated need not be known.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

Identification of a Transporter that Confers Resistance to ILs

In testing for IL resistance in a tropical rain forest soil community, a bacterium that grows in up to 8% 1-ethyl-3-methylimidazolium chloride ([C$_2$mim]Cl) was isolated. It is a Gram-negative anaerobe that is both lignocellulolytic and halotolerant: *Enterobacter lignolyticus* SCF1 (DeAngelis, et al., *Standards in Genomic Sciences* 5:69-85, 2011; Khudyakov, et al., Global transcriptome response to ionic liquid by a tropical rain forest soil bacterium, *Enterobacter lignolyticus*. *Proc. Natl. Acad. Sci USA*, 2012). We examined SCF1 to identify genes contributing to IL tolerance using various analyses, including screening an *E. coli* fosmid library containing SCF1 genomic DNA.

Methods

An SCF1 library was constructed using 30-50 kb genomic DNA inserts in fosmid vectors, and *E. coli* transformants were plated on 2% [C$_2$mim]Cl for initial selection. GFP-fluorescence was measured by flow-cytometry.

Results

Clones selected by *E. coli* growth on [C$_2$mim]Cl-agar plates were sequenced from the fosmid insertion sites and aligned to the SCF1 genome. All contained a common region of 2.6 kbp that includes only one complete gene sequence encoding MFS1, a member of the Major Facilitator Superfamily of Proteins. (FIG. 2).

Figure 3:
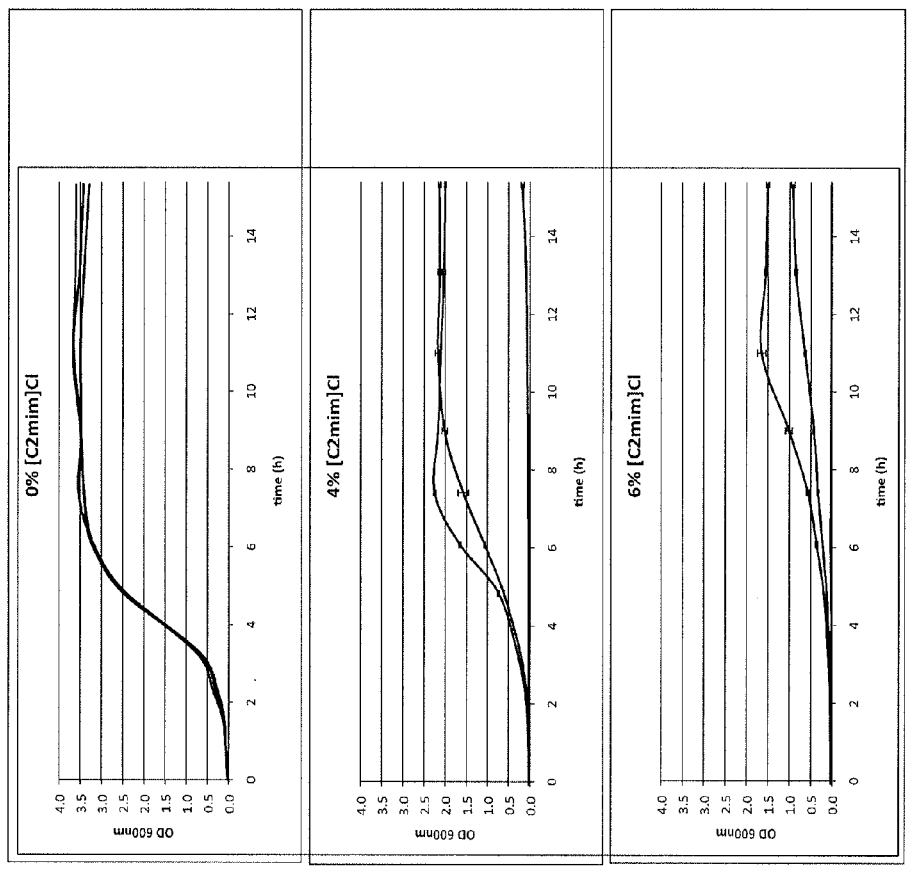
FIG. 3 provides data from a 50-ml shake flask growth assay showing the resistance of *E. coli* containing the 2606 bp region to 4% and 6% [C$_2$mim]Cl. Top panel: lines correspond to *E. coli* with common sequence; *Enterobacter lignolyticus*; and *E. coli* with empty vector; Middle panel (lines designated using hour 6 as a reference point): top line, *E. coli* with common sequence; middle line, *Enterobacter lignolyticus*; bottom line, *E. coli* with empty vector. Bottom panel: top line, *E. coli* with common sequence; middle line, *Enterobacter lignolyticus*; bottom line, *E. coli* with empty vector

SCF1 cells and *E. coli* containing an expression plasmid encoding the entire 2.6 kbp insert were tested at different levels of [C$_2$mim]Cl. The *E. coli* clones comprising the gene sequence exhibited resistance in at least 6% [C2mim]Cl (FIG. 3).

Figure 4:
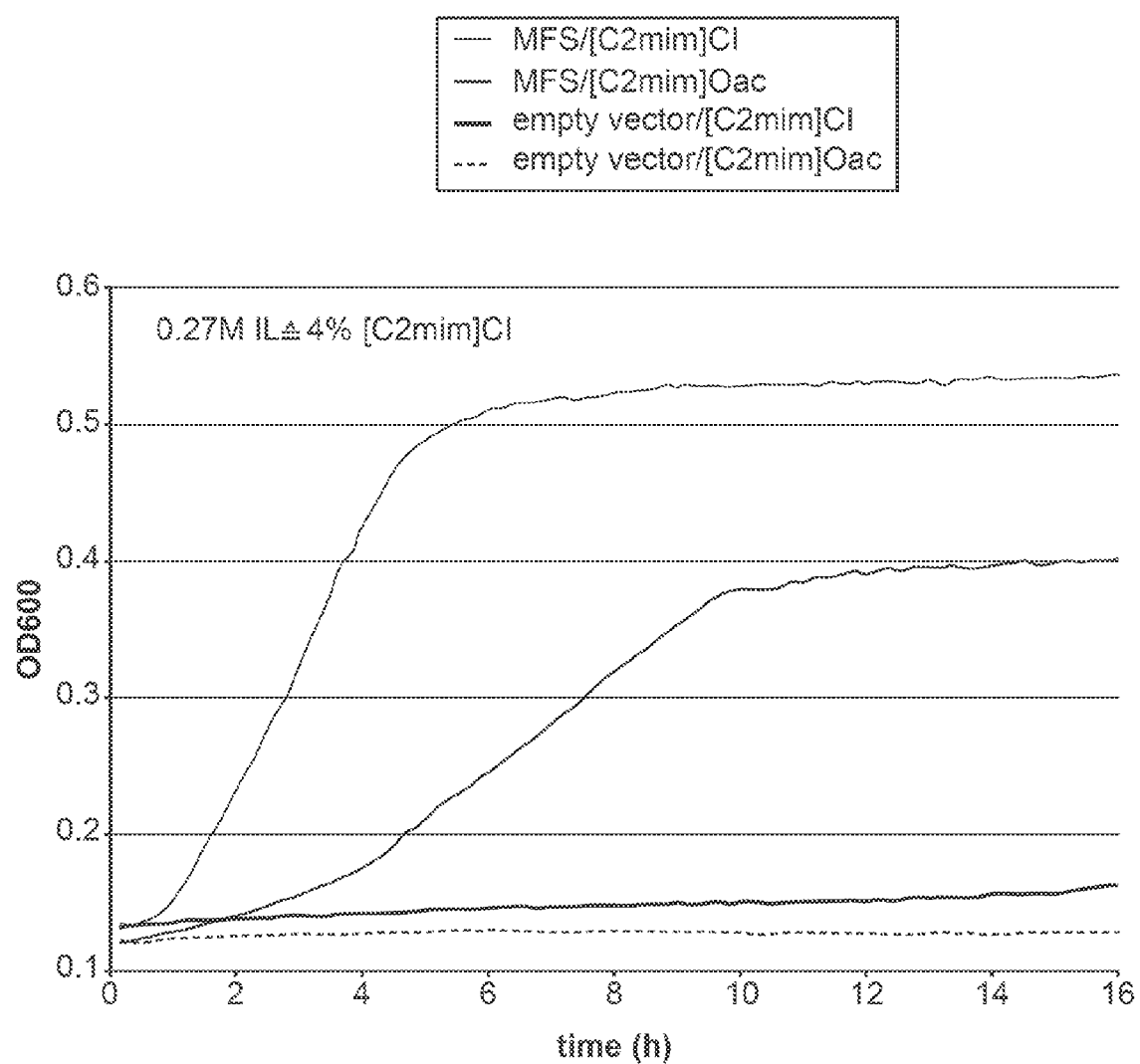
FIG. 4 presents data showing that MFS1 confers tolerance to [C$_2$mim]-Acetate in *E. coli*. Top line, MFS/[C$_2$mim]Cl; Second line from top, MFS/C$_2$mim]Oac; Second line from bottom, empty vector//[C$_2$mim]Cl; Bottom, line empty vector/C$_2$mim]Oac FIG. 5 provides illustrative data showing that [C$_2$mim]Cl-inducible TetR-repressor regulates MFS-expression.

In one experiment, *E. coli* expressing the transporter gene were also cultured in media differing only in the type of imidazolium ionic liquid (at equimolar levels), to assess the influence of aliphatic chain lengths of the cation, and the anions Cl—, BuSO4-, and acetate. In this experiment, *E. coli* exhibited tolerance to BMIM-Cl, but had lower tolerance than with EMIM-Cl (data not shown). With respect to the anion, Cl— was tolerated best and acetate less so (FIG. 4).

Figure 5:
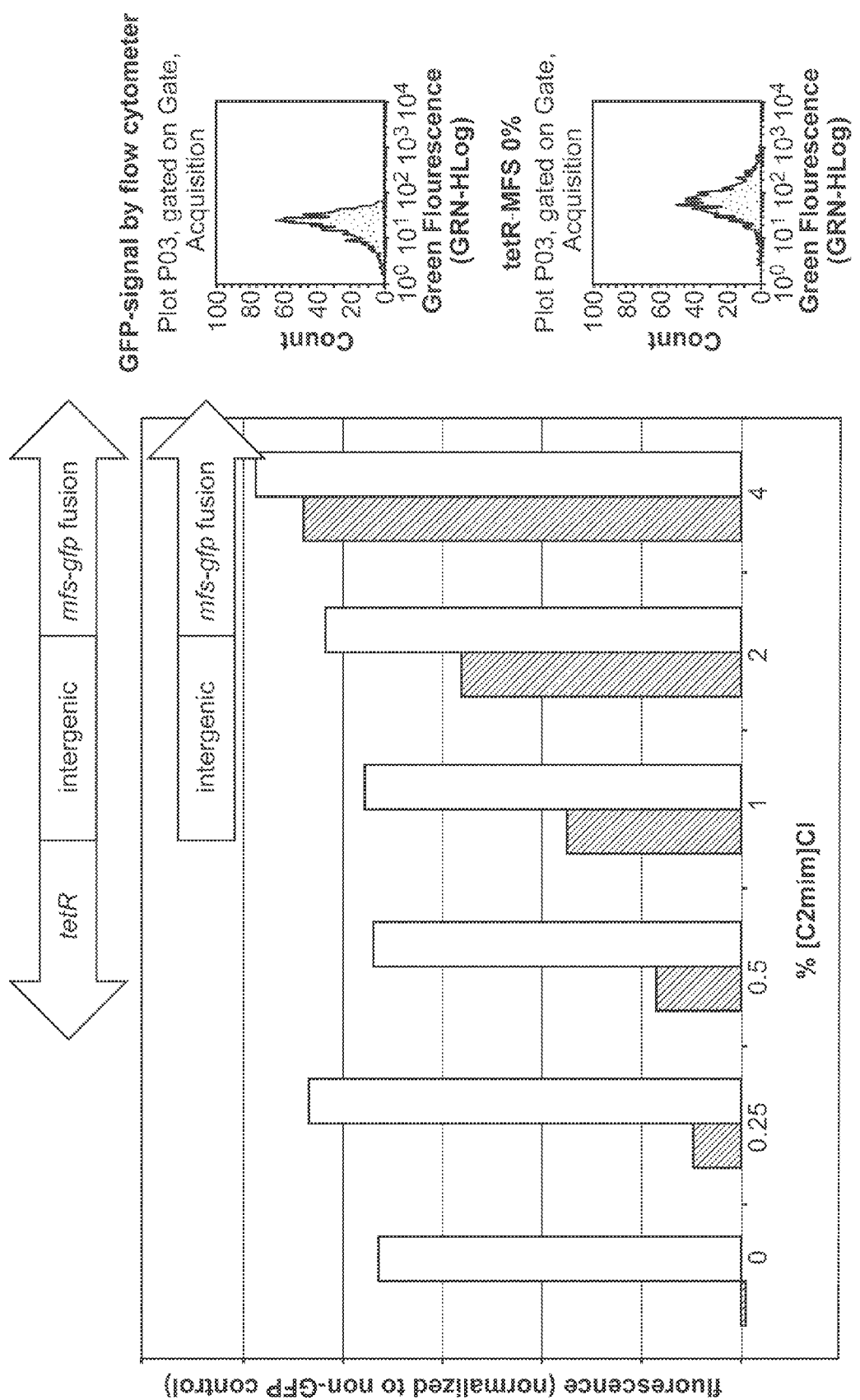
FIG. 5 shows the results of an experiment showing that the TetR-repressor (the gene encoding TetR is located adjacent to mfs1 in its native host), was inducible by [C$_2$mim]Cl, and MFS-expression was regulated by this IL. In the absence of this repressor, the intergenic promoter-region was constitutively turned on (left columns in bar graph compared to right columns).

By measuring fluorescence with an MFS1-GFP fusion protein, we found that the TetR-repressor, for which the gene that encodes it is located adjacent to mfs1 in its native host, was inducible by [C$_2$mim]Cl, and MFS1-expression was regulated by this IL (FIG. 5). In the absence of this repressor, the intergenic promoter-region was constitutively turned on.

Figure 6:
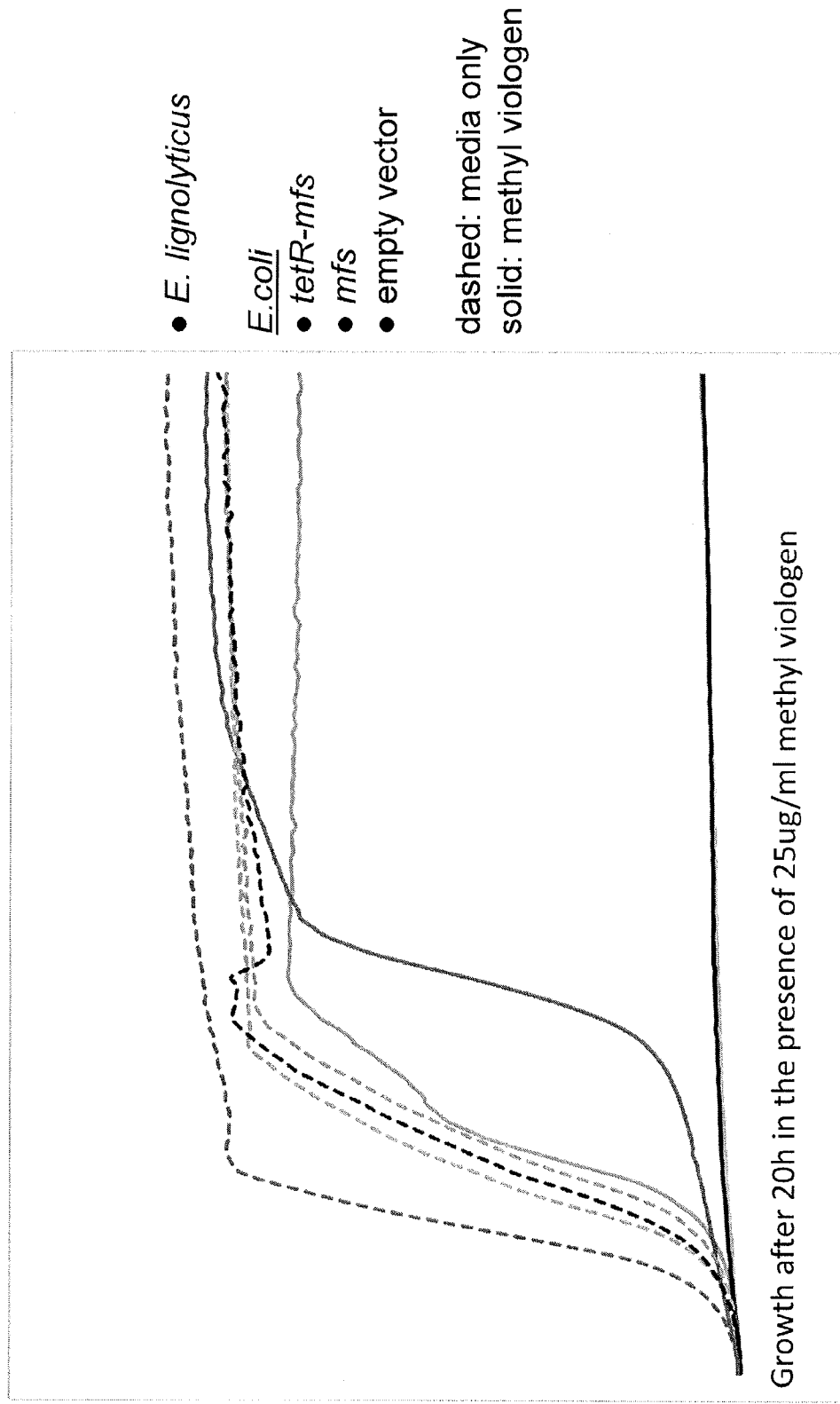
FIG. 6 shows data illustrating that MFS1 confers tolerance to methyl viologen. Bottom solid lines are empty vector and tetR-mfs.

The closest homologue of MFS1 is a methyl viologen transporter protein in *K. oxytoca*. MFS1 conferred tolerance to this compound in *E. coli* (FIG. 6).

Evaluation of *E. coli* expressing the MFS-GFP fusion protein by fluorescent microscopy showed that the protein was localized to the membrane (data not shown).

Figure 7:
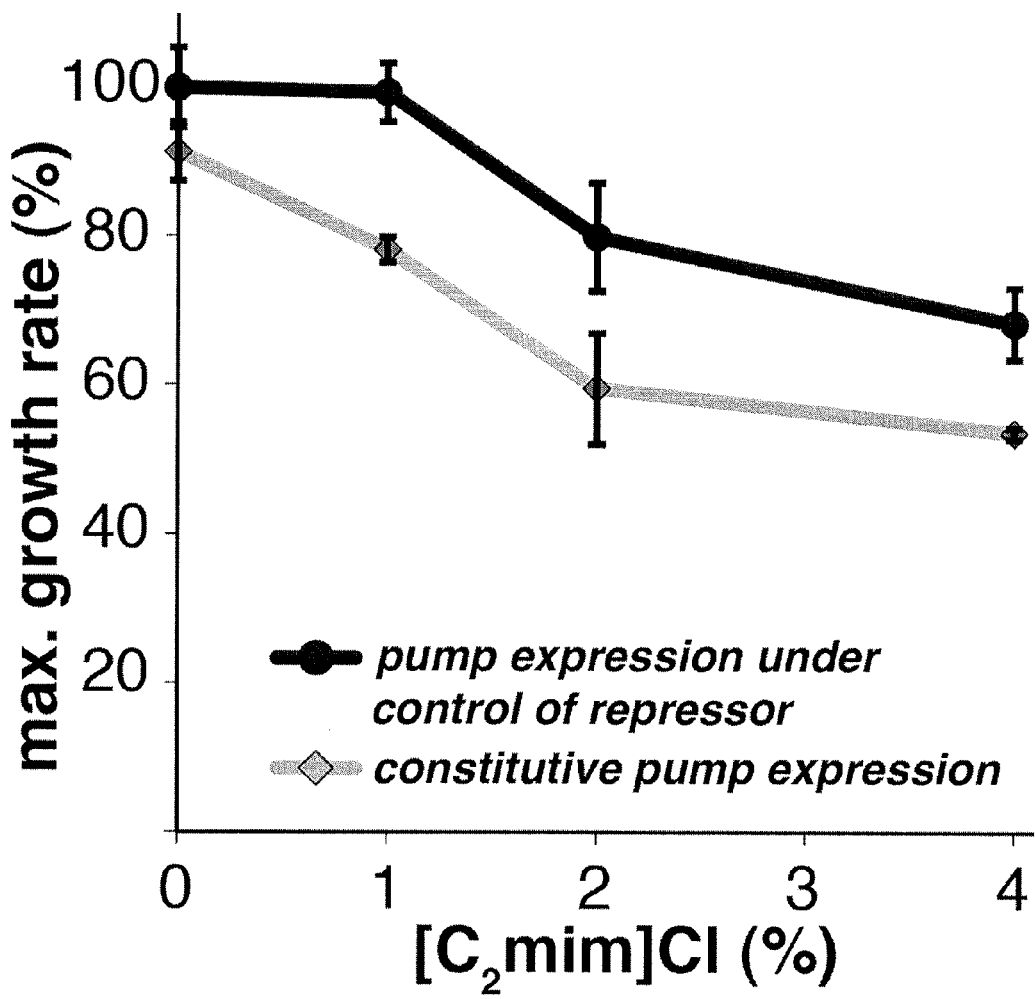
FIG. 7 provides a graph depicting illustrative data showing maximum growth rates of *E. coli* expressing the MFS1 pump protein via the native promoter, either constitutively (diamonds) or under the control of the EilR repressor (circles).

Maximum growth rates of *E. coli* that express the MFP transporter protein (also referred to as "EilA pump") in the presence of different levels of [C$_2$mim]Cl were evaluated. The *E. coli* express the MFP transporter via the native promoter either constitutively or under the control of the IL-inducible repressor protein (TetR protein, also referred to as "EilR"). The results are shown in FIG. 7. The IL-inducible repressor increased cell growth compared to constitutive pump expression.

Figure 8:
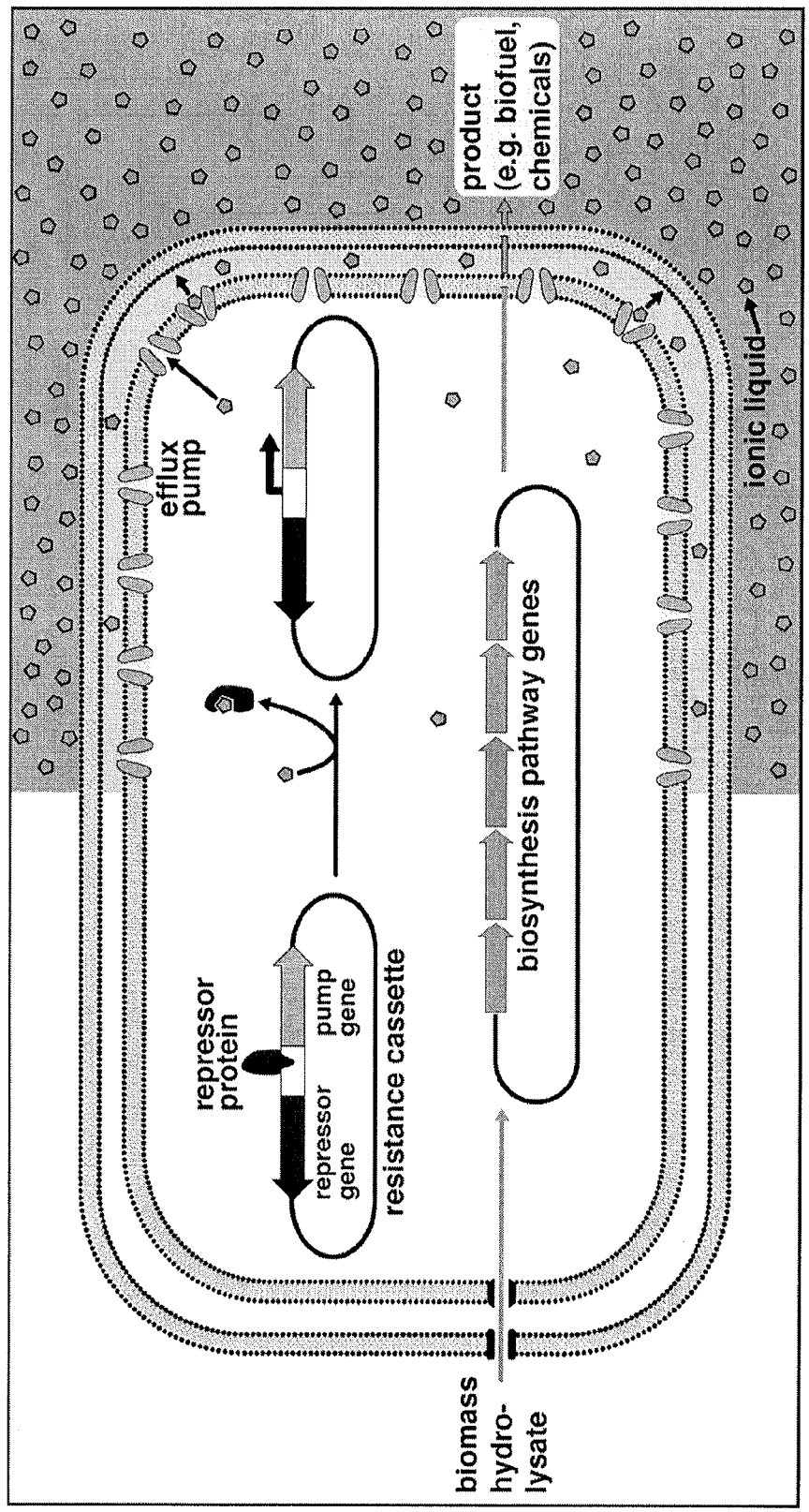
FIG. 8 provides a schematic illustrating an embodiment of the invention.

FIG. 8 provides a schematic summary of an embodiment of the invention illustrated in this example. An ionic liquid resistance cassette containing an efflux pump and a repressor gene was discovered in a soil bacterium and the genetic unit transferred to an *Escherichia coli* production strain as described in the example above. In the absence of ionic liquids (left side), transcription of the pump gene is repressed. The repressor is inducible by ionic liquids (right side), resulting in dynamic pump expression adjusting to varying ionic liquid levels. This provides for robust growth and efficient biosynthesis of biofuels and high value chemicals at ionic liquid levels that would otherwise be toxic.

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession numbers, and patent applications cited herein are hereby incorporated by reference in their entirety for all purposes.

Illustrative Sequences mfs1 gene sequence from *Enterobacter lignolyticus* strain SCF1, including upstream region; underlined = repressor (tetR); italics = intergenic promoter region; bold = mfs1 protein-coding region

SEQ ID NO: 1

TTACGAAAATAACTCAAGCTGAATAACGTGCTGCAGGTGGCGGGTGAATGCGGCATCGTC

TACCTCCGGCATTCCCAGCACGTAAATCCCGTCCAGTCCACAGACCAGCGAAATCAGCCG

CCAGGCGATATTTTCGGCGCTATCGCGCAGGGTAAATTCGCCAGCGGCATGGCCCGCGC

GAATGATCCTGACCGCTTCGTCATGCCACAGGTTCATGGTCAGCAGGTACGCGCTTTTGAT

TTCCGGATCGCTGTCGGCCAGCAGCTGCGCCTGGCGCCACAGGCGGATATAGGGCTCCA

GCCGTCCGTCCTCGCTGCCGAGGGCGGAAAACAGCTGTTCACGCCAGCCGGCGGTGCGC

GAAAGGCGCTGCAGATCCATCATCTCGCGGATCACGCGGATAAACGCCTGGGATTTTAGC

TCGCCGGAGGAGGTGAAATGGTGGTGGACCTGGCCTGCGGCGACGCCCGCGGCGGTGG

CGATGTTGCGGACCGTCATACCGGTAAACCCTTGATCCAGCGCGACGCGCATGGCGGCCT

GCATGATGGTTTCCCGACGTTCTTCGCGATTCAGATAGCCCATATCTCTCTTCCCTGGCGG

TGATAGGGCGATAATAACAAAAAGCTGGACAAGTGTTCAACTTTCCCCCACGATCGCAAAC

TGGACGGATGTCCAGCTTTGTATTTATGAGGGAGATGTATGTTTCGCCAATGGGTAACGTT

ATTTGCGATTTTGCTGGTGTATATCCCGGTCGCGATTGATGCCACCGTGCTGCACGTTGC

AGCGCCGACGCTGAGCGTATCGCTGGGGACCAGCAGCAATGAACTGTTATGGATAATCG

ATATTTATTCGCTGGTGATGGCCGGAATGGTGCTGCCGATGGGCGCGCTTGGCGATCGC

| Illustrative Sequences |
|---|
| ATCGGCTTTAAGCGCCTGCTGCTGTCCGGCAGCGGGCTGTTCGGCCTTGCCTCGCTGGC |
| GGCGGCGTTCGCCCCCAGCGCGATGTGGCTTATCGCCGCCCGCGCCTGTCTGGCCGTC |
| GGGGCGGCGATGATCGTTCCGGCGACGCTGGCGGGTATTCGCAATACCTTCAGCGAGG |
| CGCGCCACCGCAATATGGCGCTGGGGCTGTGGGCGACCATCGGTTCCGGCGGCGCAGC |
| GTTCGGCCCGCTAATCGGCGGGATTGTGCTTGAGCACTTCTGGTGGGGCGCGGTTTTCT |
| GATCAACGTACCGATCGTGCTGGTGGTGATGGCGGTTAGCGCGCGGGTCGTGCCGTGG |
| CAGCCGGGGCGGCGCGAGCAGCCGCTGAACTTTACCCACGCGGTTCATGCTGGTGGCGG |
| CGATTCTGCTGCTGGTGTGGAGCGCCAAATCGGCGATCAAGGGCAGCGAAGGGCTGGG |
| GTTTGTTGCGCTGGCGCTGCTGGTGGGCGGCGTACTGCTGACGGCCTTCGTGCGCATTC |
| AGCTGGCGGCGCGTACGCCGATGATCGACATGCGGCTGTTCACCCACCGTATTATCCTC |
| TGCGGCGTGATGATGGCGATAACCGCGCTGGCGACGCTGGTGGGCTTTGAGCTGCTGAT |
| GGCGCAGGAGCTGCAGTTTGTGCACGGCAAAACGCCGTTCGAAGCGGGGCTGTTTATGC |
| TGCCGGTGATGCTGGCGAGCGGTTTTAGCGGCCCCATCGCCGGAATACTGGTGTCGCGC |
| ATTGGTTTGCGTGAAGTGGCGACCGGCGGCATGATGCTCAGCGCGTTAAGTTTCCTCGG |
| ACTGTCGATGACCGATTTTACCACCCAGCAGTGGCAGGCCTGGGGGCTGATGACGATGC |
| TGGGCTTCAGCGCCGCCAGCGCGCTGCTGGCCTCAACGGCGGCGATAATGGCGGCGGC |
| GCCGAAAGAAAAAGCGGCCGCGGCCGGGGCTATCGAAACCATGGCCTACGAGCTTGGC |
| GCCGGGCTGGGTATTGCGGTGTTCGGTCTGATCCTCACCCGCAGCTACAGCGGCTCTAT |
| TTTGCTGCCGGACGGGCTGCTGGCCGGGGAAGCGGCGCGGGCGTCGTCGTCTATCGGC |
| GAGGCGGTACAGCTGGCGCAGACGCTGGAGCAGCCGCAGGCGATGGCGGTCATCGAC |
| GCGGCGAAAACCGCGTTTATTTCATCGCACAGCGTGGTGCTGTTCAGCGCCGGGGGAAT |
| GCTGCTGGCGCTGGCGGTCGGCGTCTGGTTCGGCCTGGCAAAGGTGCGCCAGACCGCG |
| TGA |

Enterobacter lignolyticus protein sequence
SEQ ID NO: 2
MFRQWVTLFAILLVYIPVAIDATVLHVAAPTLSVSLGTSSNELLWIIDIYSLVMAGMVLPMGALGDRIGF
KRLLLSGSGLFGLASLAAAFAPSAMWLIAARACLAVGAAMIVPATLAGIRNTFSEARHRNMALGLWATIG
SGGAAFGPLIGGIVLEHFWWGAVFLINVPIVLVVMAVSARVVPWQPGRREQPLNFTHAVMLVAAILLLVW
SAKSAIKGSEGLGFVALALLVGGVLLTAFVRIQLAARTPMIDMRLFTHRIILCGVMMAITALATLVGFEL
LMAQELQFVHGKTPFEAGLFMLPVMLASGFSGPIAGILVSRIGLREVATGGMMLSALSFLGLSMTDFTTQ
QWQAWGLMTMLGFSAASALLASTAAIMAAAPKEKAAAAGAIETMAYELGAGLGIAVFGLILTRSYSGSIL
LPDGLLAGEAARASSSIGEAVQLAQTLEQPQAMAVIDAAKTAFISSHSVVLFSAGGMLLALAVGVWFGLA
KVRQTA*

What is claimed is:

1. A method of increasing the yield from a reaction in which soluble sugars are a source of carbon, the method comprising incubating a microorganism with biomass pretreated with an ionic liquid, wherein the biomass pretreated with an ionic liquid provides a source of soluble sugars as a carbon source, wherein the microorganism comprises a heterologous gene encoding a Major Facilitator Superfamily 1 (MFS 1) polypeptide operably linked to a promoter, wherein said MFS 1 polypeptide has an amino acid sequence with at least 95% sequence identity to the amino acid sequence set forth in SEQ ID NO:2, and wherein said MFS 1 polypeptide facilitates resistance of the microorganism to said ionic liquid as compared to a microorganism without said heterologous gene.

2. The method of claim 1, wherein said biomass is incubated with said microorganism in a fermentation reaction that produces an alcohol.

3. The method of claim 1, wherein said MFS 1 polypeptide comprises the amino acid sequence of SEQ ID NO:2.

4. The method of claim 1, wherein said heterologous gene is operably linked to a tet repressor sequence.

5. The method of claim 4, wherein said microorganism is genetically modified to express a tet repressor protein that binds to the tet repressor sequence.

6. The method of claim 1, wherein said microorganism is a bacteria.

7. The method of claim 6, wherein said bacteria is *Escherichia coli*.

8. The method of claim 1, wherein said microorganism is a yeast or a filamentous fungi.

9. The method of claim 1, wherein said ionic liquid comprises an anion, wherein said anion is Cl— or acetate.

10. The method of claim 1, wherein said heterologous gene encoding said MFS 1 polypeptide is integrated into the genome of said microorganism.

11. The method of claim 1, wherein said microorganism is generated by transforming said microorganism with an expression cassette, wherein the said expression cassette comprises said heterologous gene encoding said MFS 1 polypeptide.

* * * * *

SEQUENCE LISTING

<160> NUMBER OF SEQ ID NOS: 29

<210> SEQ ID NO 1
<211> LENGTH: 2187
<212> TYPE: DNA
<213> ORGANISM: Enterobacter lignolyticus
<220> FEATURE:

<223> OTHER INFORMATION: Enterobacter lignolyticus strain SCF1 Major
      Facilitator Superfamily 1 (MFS1)
<220> FEATURE:
<221> NAME/KEY: CDS
<222> LOCATION: (697)...(2187)
<223> OTHER INFORMATION: MFS1

<400> SEQUENCE: 1

```
ttacgaaaat aactcaagct gaataacgtg ctgcaggtgg cgggtgaatg cggcatcgtc      60
tacctccggc attcccagca cgtaaatccc gtccagtcca cagaccagcg aaatcagccg     120
ccaggcgata ttttcggcgc tatcgcgcag ggtaaattcg ccagcggcat ggcccgcgcg     180
aatgatcctg accgcttcgt catgccacag gttcatggtc agcaggtacg cgcttttgat     240
ttccggatcg ctgtcggcca gcagctgcgc ctggcgccac aggcggatat agggctccag     300
ccgtccgtcc tcgctgccga gggcggaaaa cagctgttca cgccagccgg cggtgcgcga     360
aaggcgctgc agatccatca tctcgcggat cacgcggata aacgcctggg attttagctc     420
gccggaggag gtgaaatggt ggtggacctg gcctgcggcg acgcccgcgg cggtggcgat     480
gttgcggacc gtcataccgg taaacccttg atccagcgcg acgcgcatgg cggcctgcat     540
gatggtttcc cgacgttctt cgcgattcag atagcccata tctctcttcc ctggcggtga     600
tagggcgata ataacaaaaa gctggacaag tgttcaactt tccccacga tcgcaaactg      660 gacgatgtc cagctttgta tttatgaggg agatgtatgt ttcgccaatg ggtaacgtta     720
tttgcgattt tgctggtgta tcccggtc gcgattgatg ccaccgtgct gcacgttgca     780
gcgccgacgc tgagcgtatc gctggggacc agcagcaatg aactgttatg gataatcgat     840
atttattcgc tggtgatggc cggaatggtg ctgccgatgg gcgcgcttgg cgatcgcatc     900
ggctttaagc gcctgctgct gtccggcagc gggctgttcg gccttgcctc gctggcggcg     960
gcgttcgccc ccagcgcgat gtggcttatc gccgcccgcg cctgtctggc cgtcggggcg    1020
gcgatgatcg ttccggcgac gctggcgggt attcgcaata ccttcagcga ggcgcgccac    1080
cgcaatatgg cgctggggct gtgggcgacc atcggttccg gcggcgcagc gttcggcccg    1140
ctaatcggcg ggattgtgct tgagcacttc tggtggggcg cggttttctc tgatcaacgta   1200 ccgatcgtgc tggtggtgat ggcggttagc gcgcgggtcg tgccgtggca gccggggcgg    1260
cgcgagcagc cgctgaactt tacccacgcg gtcatgctgg tggcggcgat tctgctgctg    1320
gtgtggagcg ccaaatcggc gatcaagggc agcgaagggc tggggtttgt tgcgctggcg    1380
ctgctggtgg cggcgtact gctgacggcc ttcgtgcgca ttcagctggc ggcgcgtacg    1440
ccgatgatcg acatgcggct gttcacccac cgtattatcc tctgcggcgt gatgatggcg    1500
ataaccgcgc tggcgacgct ggtgggcttt gagctgctga tggcgcagga gctgcagttt    1560
gtgcacggca aaacgccgtt cgaagcgggg ctgtttatgc tgccggtgat gctggcgagc    1620
ggttttagcg gccccatcgc cggaatactg gtgtcgcgca ttggtttgcg tgaagtggcg    1680
accggcggca tgatgctcag cgcgttaagt ttcctcggac tgtcgatgac cgattttacc    1740
acccagcagt ggcaggcctg ggggctgatg acgatgctgg gcttcagcgc cgccagcgcg    1800
ctgctggcct caacgcggc gataatggcg cggcgccga agaaaaagc ggccgcggcc     1860 ggggctatcg aaaccatggc ctacgagctt ggcgccgggc tgggtattgc ggtgttcggt    1920
ctgatcctca cccgcagcta cagcggctct attttgctgc cggacgggct gctggccggg    1980
gaagcggcgc gggcgtcgtc gtctatcggc gaggcggtac agctggcgca gacgctggag    2040
cagccgcagg cgatggcggt catcgacgcg gcgaaaaccg cgtttatttc atcgcacagc    2100
```

```
gtggtgctgt tcagcgccgg gggaatgctg ctggcgctgg cggtcggcgt ctggttcggc    2160
ctggcaaagg tgcgccagac cgcgtga                                         2187
```

<210> SEQ ID NO 2
<211> LENGTH: 496
<212> TYPE: PRT
<213> ORGANISM: Enterobacter lignolyticus
<220> FEATURE:
<223> OTHER INFORMATION: Enterobacter lignolyticus strain SCF1 Major
      Facilitator Superfamily 1 (MFS1)

<400> SEQUENCE: 2

| Met | Phe | Arg | Gln | Trp | Val | Thr | Leu | Phe | Ala | Ile | Leu | Leu | Val | Tyr | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Pro Val Ala Ile Asp Ala Thr Val Leu His Val Ala Ala Pro Thr Leu
            20                  25                  30

Ser Val Ser Leu Gly Thr Ser Ser Asn Glu Leu Leu Trp Ile Ile Asp
        35                  40                  45

Ile Tyr Ser Leu Val Met Ala Gly Met Val Leu Pro Met Gly Ala Leu
    50                  55                  60

Gly Asp Arg Ile Gly Phe Lys Arg Leu Leu Ser Gly Ser Gly Leu
65                  70                  75                  80

Phe Gly Leu Ala Ser Leu Ala Ala Ala Phe Ala Pro Ser Ala Met Trp
                85                  90                  95

Leu Ile Ala Ala Arg Ala Cys Leu Ala Val Gly Ala Ala Met Ile Val
            100                 105                 110

Pro Ala Thr Leu Ala Gly Ile Arg Asn Thr Phe Ser Glu Ala Arg His
        115                 120                 125

Arg Asn Met Ala Leu Gly Leu Trp Ala Thr Ile Gly Ser Gly Gly Ala
    130                 135                 140

Ala Phe Gly Pro Leu Ile Gly Gly Ile Val Leu Glu His Phe Trp Trp
145                 150                 155                 160

Gly Ala Val Phe Leu Ile Asn Val Pro Ile Val Leu Val Val Met Ala
                165                 170                 175

Val Ser Ala Arg Val Val Pro Trp Gln Pro Gly Arg Arg Glu Gln Pro
            180                 185                 190

Leu Asn Phe Thr His Ala Val Met Leu Val Ala Ala Ile Leu Leu Leu
        195                 200                 205

Val Trp Ser Ala Lys Ser Ala Ile Lys Gly Ser Glu Gly Leu Gly Phe
    210                 215                 220

Val Ala Leu Ala Leu Leu Val Gly Gly Val Leu Leu Thr Ala Phe Val
225                 230                 235                 240

Arg Ile Gln Leu Ala Ala Arg Thr Pro Met Ile Asp Met Arg Leu Phe
                245                 250                 255

Thr His Arg Ile Ile Leu Cys Gly Val Met Met Ala Ile Thr Ala Leu
            260                 265                 270

Ala Thr Leu Val Gly Phe Glu Leu Leu Met Ala Gln Glu Leu Gln Phe
        275                 280                 285

Val His Gly Lys Thr Pro Phe Glu Ala Gly Leu Phe Met Leu Pro Val
    290                 295                 300

Met Leu Ala Ser Gly Phe Ser Gly Pro Ile Ala Gly Ile Leu Val Ser
305                 310                 315                 320

Arg Ile Gly Leu Arg Glu Val Ala Thr Gly Gly Met Met Leu Ser Ala
                325                 330                 335

Leu Ser Phe Leu Gly Leu Ser Met Thr Asp Phe Thr Thr Gln Gln Trp

```
                    340               345               350
Gln Ala Trp Gly Leu Met Thr Met Leu Gly Phe Ser Ala Ala Ser Ala
            355                   360                   365
Leu Leu Ala Ser Thr Ala Ala Ile Met Ala Ala Pro Lys Glu Lys
        370                   375                   380
Ala Ala Ala Ala Gly Ala Ile Glu Thr Met Ala Tyr Glu Leu Gly Ala
385                   390                   395                   400
Gly Leu Gly Ile Ala Val Phe Gly Leu Ile Leu Thr Arg Ser Tyr Ser
                    405                   410                   415
Gly Ser Ile Leu Leu Pro Asp Gly Leu Leu Ala Gly Glu Ala Ala Arg
                420                   425                   430
Ala Ser Ser Ser Ile Gly Glu Ala Val Gln Leu Ala Gln Thr Leu Glu
            435                   440                   445
Gln Pro Gln Ala Met Ala Val Ile Asp Ala Ala Lys Thr Ala Phe Ile
        450                   455                   460
Ser Ser His Ser Val Val Leu Phe Ser Ala Gly Gly Met Leu Leu Ala
465                   470                   475                   480
Leu Ala Val Gly Val Trp Phe Gly Leu Ala Lys Val Arg Gln Thr Ala
                    485                   490                   495

<210> SEQ ID NO 3
<211> LENGTH: 491
<212> TYPE: PRT
<213> ORGANISM: Enterobacter lignolyticus
<220> FEATURE:
<223> OTHER INFORMATION: Enterobacter lignolyticus strain SCF1 Major
      Facilitator Superfamily 1 (MFS1)

<400> SEQUENCE: 3

Met Phe Arg Gln Trp Val Thr Leu Phe Ala Ile Leu Leu Val Tyr Ile
1               5                   10                  15
Pro Val Ala Ile Asp Ala Thr Val Leu His Val Ala Ala Pro Thr Leu
            20                  25                  30
Ser Val Ser Leu Gly Thr Ser Ser Asn Glu Leu Leu Trp Ile Ile Asp
        35                  40                  45
Ile Tyr Ser Leu Val Met Ala Gly Met Val Leu Pro Met Gly Ala Leu
    50                  55                  60
Gly Asp Arg Ile Gly Phe Lys Arg Leu Leu Leu Ser Gly Ser Gly Leu
65                  70                  75                  80
Phe Gly Leu Ala Ser Leu Ala Ala Ala Phe Ala Pro Ser Ala Met Trp
                85                  90                  95
Leu Ile Ala Ala Arg Ala Cys Leu Ala Val Gly Ala Ala Met Ile Val
            100                 105                 110
Pro Ala Thr Leu Ala Gly Ile Arg Asn Thr Phe Ser Glu Ala Arg His
        115                 120                 125
Arg Asn Met Ala Leu Gly Leu Trp Ala Thr Ile Gly Ser Gly Gly Ala
    130                 135                 140
Ala Phe Gly Pro Leu Ile Gly Gly Ile Val Leu Glu His Phe Trp Trp
145                 150                 155                 160
Gly Ala Val Phe Leu Ile Asn Val Pro Ile Val Leu Val Met Ala
                165                 170                 175
Val Ser Ala Arg Val Val Pro Trp Gln Pro Gly Arg Arg Glu Gln Pro
            180                 185                 190
Leu Asn Phe Thr His Ala Val Met Leu Val Ala Ala Ile Leu Leu Leu
        195                 200                 205
```

```
Val Trp Ser Ala Lys Ser Ala Ile Lys Gly Ser Glu Gly Leu Gly Phe
210                 215                 220

Val Ala Leu Ala Leu Leu Val Gly Gly Val Leu Leu Thr Ala Phe Val
225                 230                 235                 240

Arg Ile Gln Leu Ala Ala Arg Thr Pro Met Ile Asp Met Arg Leu Phe
                245                 250                 255

Thr His Arg Ile Ile Leu Cys Gly Val Met Met Ala Ile Thr Ala Leu
                260                 265                 270

Ala Thr Leu Val Gly Phe Glu Leu Met Ala Gln Glu Leu Gln Phe
            275                 280                 285

Val His Gly Lys Thr Pro Phe Glu Ala Gly Leu Phe Met Leu Pro Val
290                 295                 300

Met Leu Ala Ser Gly Phe Ser Gly Pro Ile Ala Gly Ile Leu Val Ser
305                 310                 315                 320

Arg Ile Gly Leu Arg Glu Val Ala Thr Gly Met Met Leu Ser Ala
                325                 330                 335

Leu Ser Phe Leu Gly Leu Ser Met Thr Asp Phe Thr Gln Gln Trp
            340                 345                 350

Gln Ala Trp Gly Leu Met Thr Met Leu Gly Phe Ser Ala Ala Ser Ala
                355                 360                 365

Leu Leu Ala Ser Thr Ala Ala Ile Met Ala Ala Pro Lys Glu Lys
370                 375                 380

Ala Ala Ala Ala Gly Ala Ile Glu Thr Met Ala Tyr Glu Leu Gly Ala
385                 390                 395                 400

Gly Leu Gly Ile Ala Val Phe Gly Leu Ile Leu Thr Arg Ser Tyr Ser
                405                 410                 415

Gly Ser Ile Leu Leu Pro Asp Gly Leu Leu Ala Gly Glu Ala Ala Arg
                420                 425                 430

Ala Ser Ser Ser Ile Gly Glu Ala Val Gln Leu Ala Gln Thr Leu Glu
                435                 440                 445

Gln Pro Gln Ala Met Ala Val Ile Asp Ala Ala Lys Thr Ala Phe Ile
                450                 455                 460

Ser Ser His Ser Val Val Leu Phe Ser Ala Gly Gly Met Leu Leu Ala
465                 470                 475                 480

Leu Ala Val Gly Val Trp Phe Gly Leu Ala Lys
                485                 490

<210> SEQ ID NO 4
<211> LENGTH: 491
<212> TYPE: PRT
<213> ORGANISM: Klebsiella oxytoca
<220> FEATURE:
<223> OTHER INFORMATION: methyl viologen resistance protein smvA

<400> SEQUENCE: 4

Met Ser Arg Gln Trp Leu Thr Leu Val Ala Ile Leu Leu Val Tyr Leu
1               5                   10                  15

Pro Val Ala Ile Asp Ala Thr Val Leu His Val Ala Ala Pro Thr Leu
                20                  25                  30

Ser Met Ser Leu Gly Thr Ser Ser Asn Glu Leu Leu Trp Ile Ile Asp
            35                  40                  45

Ile Tyr Ser Leu Val Met Ala Gly Met Val Leu Pro Met Gly Ala Leu
        50                  55                  60

Gly Asp Lys Ile Gly Phe Lys Arg Leu Leu Leu Gly Ser Ala Ile
65                  70                  75                  80
```

```
Phe Gly Val Ser Ser Leu Ala Ala Phe Ser Pro Thr Ala Leu Ala
                85                  90                  95

Leu Ile Ala Ser Arg Ala Leu Leu Ala Ile Gly Ala Ala Met Ile Val
            100                 105                 110

Pro Ala Thr Leu Ala Gly Ile Arg Asn Thr Phe Ser Gln Ala Arg His
        115                 120                 125

Arg Asn Met Ala Leu Gly Leu Trp Ala Ala Ile Gly Ser Gly Gly Ala
    130                 135                 140

Ala Phe Gly Pro Leu Val Gly Gly Ile Leu Leu Glu His Phe Tyr Trp
145                 150                 155                 160

Gly Ser Val Phe Leu Ile Asn Val Pro Ile Val Leu Ala Val Ile Ala
                165                 170                 175

Phe Ser Ala Arg Met Val Pro Arg Gln Pro Ala Arg Arg Glu Gln Pro
            180                 185                 190

Leu Asn Leu Thr Gln Ala Leu Met Leu Ile Val Ala Ile Leu Met Leu
        195                 200                 205

Val Phe Ser Ala Lys Ser Ala Leu Lys Gly Gln Met Ala Leu Trp Leu
    210                 215                 220

Thr Gly Ser Ile Ala Leu Val Gly Leu Ala Leu Leu Val Arg Phe Val
225                 230                 235                 240

Arg Gln Gln Leu Ser Ala Ala Thr Pro Met Val Asp Met Arg Leu Phe
                245                 250                 255

Thr His Arg Ile Ile Leu Ser Gly Val Met Met Ala Met Thr Ala Leu
            260                 265                 270

Ile Thr Leu Val Gly Phe Glu Leu Leu Met Ala Gln Glu Leu Gln Phe
        275                 280                 285

Val His Gly Lys Thr Pro Phe Glu Ala Gly Leu Phe Met Leu Pro Leu
    290                 295                 300

Met Leu Ala Ser Gly Phe Ser Gly Pro Val Ala Gly Val Met Val Ser
305                 310                 315                 320

Arg Leu Gly Leu Arg Leu Val Ala Thr Gly Met Leu Leu Ser Ala
                325                 330                 335

Leu Ser Phe Leu Gly Leu Ser Met Thr Asp Phe Ser Ser Gln Gln Trp
            340                 345                 350

Leu Ala Trp Gly Leu Met Ile Leu Leu Gly Phe Ser Val Ala Ser Ala
        355                 360                 365

Leu Leu Ala Ser Gly Ser Ala Ile Met Ala Ala Pro Lys Glu Lys
    370                 375                 380

Ala Ala Ala Ala Gly Ala Ile Glu Thr Met Ala Tyr Glu Leu Gly Ala
385                 390                 395                 400

Gly Leu Gly Ile Ala Leu Phe Gly Leu Ile Leu Thr Arg Ser Tyr Ser
                405                 410                 415

Ser Ser Ile Val Leu Pro Ala Gly Val Asp Gly Gln Ala Ala Ala Gln
            420                 425                 430

Ala Ser Ser Ser Ile Ser Glu Ala Ile Ala Leu Ala Gln Ser Leu Pro
        435                 440                 445

Ala Val Pro Ala His Ser Leu Ile Ala Ala Lys Thr Ala Phe Ile
    450                 455                 460

Ser Ala His Ser Ile Val Leu Ala Thr Ala Gly Val Leu Leu Leu Leu
465                 470                 475                 480

Leu Ala Ala Gly Ile Trp Arg Ser Leu Ala Gln
                485                 490
```

-continued

```
<210> SEQ ID NO 5
<211> LENGTH: 6
<212> TYPE: PRT
<213> ORGANISM: Artificial Sequence
<220> FEATURE:
<223> OTHER INFORMATION: synthetic consensus peptide

<400> SEQUENCE: 5

Ala Ile Leu Leu Val Tyr
1               5

<210> SEQ ID NO 6
<211> LENGTH: 17
<212> TYPE: PRT
<213> ORGANISM: Artificial Sequence
<220> FEATURE:
<223> OTHER INFORMATION: synthetic consensus peptide

<400> SEQUENCE: 6

Pro Val Ala Ile Asp Ala Thr Val Leu His Val Ala Ala Pro Thr Leu
1               5                   10                  15

Ser

<210> SEQ ID NO 7
<211> LENGTH: 32
<212> TYPE: PRT
<213> ORGANISM: Artificial Sequence
<220> FEATURE:
<223> OTHER INFORMATION: synthetic consensus peptide

<400> SEQUENCE: 7

Ser Leu Gly Thr Ser Ser Asn Glu Leu Leu Trp Ile Ile Asp Ile Tyr
1               5                   10                  15

Ser Leu Val Met Ala Gly Met Val Leu Pro Met Gly Ala Leu Gly Asp
            20                  25                  30

<210> SEQ ID NO 8
<211> LENGTH: 8
<212> TYPE: PRT
<213> ORGANISM: Artificial Sequence
<220> FEATURE:
<223> OTHER INFORMATION: synthetic consensus peptide

<400> SEQUENCE: 8

Ile Gly Phe Lys Arg Leu Leu Leu
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic consensus peptide

<400> SEQUENCE: 9

Ser Leu Ala Ala Ala Phe
1               5

<210> SEQ ID NO 10
<211> LENGTH: 18
<212> TYPE: PRT
<213> ORGANISM: Artificial Sequence
<220> FEATURE:
<223> OTHER INFORMATION: synthetic consensus peptide

<400> SEQUENCE: 10
```

```
Gly Ala Ala Met Ile Val Pro Ala Thr Leu Ala Gly Ile Arg Asn Thr
 1               5                  10                  15
Phe Ser

<210> SEQ ID NO 11
<211> LENGTH: 12
<212> TYPE: PRT
<213> ORGANISM: Artificial Sequence
<220> FEATURE:
<223> OTHER INFORMATION: synthetic consensus peptide

<400> SEQUENCE: 11

Ala Arg His Arg Asn Met Ala Leu Gly Leu Trp Ala
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: synthetic consensus peptide

<400> SEQUENCE: 12

Ile Gly Ser Gly Gly Ala Ala Phe Gly Pro Leu
 1               5                  10

<210> SEQ ID NO 13
<211> LENGTH: 4
<212> TYPE: PRT
<213> ORGANISM: Artificial Sequence
<220> FEATURE:
<223> OTHER INFORMATION: synthetic consensus peptide

<400> SEQUENCE: 13

Leu Glu His Phe
 1

<210> SEQ ID NO 14
<211> LENGTH: 10
<212> TYPE: PRT
<213> ORGANISM: Artificial Sequence
<220> FEATURE:
<223> OTHER INFORMATION: synthetic consensus peptide

<400> SEQUENCE: 14

Val Phe Leu Ile Asn Val Pro Ile Val Leu
 1               5                  10

<210> SEQ ID NO 15
<211> LENGTH: 7
<212> TYPE: PRT
<213> ORGANISM: Artificial Sequence
<220> FEATURE:
<223> OTHER INFORMATION: synthetic consensus peptide

<400> SEQUENCE: 15

Arg Arg Glu Gln Pro Leu Asn
 1               5

<210> SEQ ID NO 16
<211> LENGTH: 5
<212> TYPE: PRT
<213> ORGANISM: Artificial Sequence
<220> FEATURE:
<223> OTHER INFORMATION: synthetic consensus peptide

<400> SEQUENCE: 16
```

```
Ser Ala Lys Ser Ala
1               5

<210> SEQ ID NO 17
<211> LENGTH: 11
<212> TYPE: PRT
<213> ORGANISM: Artificial Sequence
<220> FEATURE:
<223> OTHER INFORMATION: synthetic consensus peptide

<400> SEQUENCE: 17

Asp Met Arg Leu Phe Thr His Arg Ile Ile Leu
1               5                   10

<210> SEQ ID NO 18
<211> LENGTH: 5
<212> TYPE: PRT
<213> ORGANISM: Artificial Sequence
<220> FEATURE:
<223> OTHER INFORMATION: synthetic consensus peptide

<400> SEQUENCE: 18

Gly Val Met Met Ala
1               5

<210> SEQ ID NO 19
<211> LENGTH: 30
<212> TYPE: PRT
<213> ORGANISM: Artificial Sequence
<220> FEATURE:
<223> OTHER INFORMATION: synthetic consensus peptide

<400> SEQUENCE: 19

Thr Leu Val Gly Phe Glu Leu Leu Met Ala Gln Glu Leu Gln Phe Val
1               5                   10                  15

His Gly Lys Thr Pro Phe Glu Ala Gly Leu Phe Met Leu Pro
            20                  25                  30

<210> SEQ ID NO 20
<211> LENGTH: 9
<212> TYPE: PRT
<213> ORGANISM: Artificial Sequence
<220> FEATURE:
<223> OTHER INFORMATION: synthetic consensus peptide

<400> SEQUENCE: 20

Met Leu Ala Ser Gly Phe Ser Gly Pro
1               5

<210> SEQ ID NO 21
<211> LENGTH: 6
<212> TYPE: PRT
<213> ORGANISM: Artificial Sequence
<220> FEATURE:
<223> OTHER INFORMATION: synthetic consensus peptide

<400> SEQUENCE: 21

Val Ala Thr Gly Gly Met
1               5

<210> SEQ ID NO 22
<211> LENGTH: 14
<212> TYPE: PRT
<213> ORGANISM: Artificial Sequence
<220> FEATURE:
<223> OTHER INFORMATION: synthetic consensus peptide
```

<400> SEQUENCE: 22

Leu Ser Ala Leu Ser Phe Leu Gly Leu Ser Met Thr Asp Phe
1               5                   10

<210> SEQ ID NO 23
<211> LENGTH: 5
<212> TYPE: PRT
<213> ORGANISM: Artificial Sequence
<220> FEATURE:
<223> OTHER INFORMATION: synthetic consensus peptide

<400> SEQUENCE: 23

Ala Trp Gly Leu Met
1               5

<210> SEQ ID NO 24
<211> LENGTH: 4
<212> TYPE: PRT
<213> ORGANISM: Artificial Sequence
<220> FEATURE:
<223> OTHER INFORMATION: synthetic consensus peptide

<400> SEQUENCE: 24

Leu Gly Phe Ser
1

<210> SEQ ID NO 25
<211> LENGTH: 7
<212> TYPE: PRT
<213> ORGANISM: Artificial Sequence
<220> FEATURE:
<223> OTHER INFORMATION: synthetic consensus peptide

<400> SEQUENCE: 25

Ala Ser Ala Leu Leu Ala Ser
1               5

<210> SEQ ID NO 26
<211> LENGTH: 31
<212> TYPE: PRT
<213> ORGANISM: Artificial Sequence
<220> FEATURE:
<223> OTHER INFORMATION: synthetic consensus peptide

<400> SEQUENCE: 26

Ala Ile Met Ala Ala Ala Pro Lys Glu Lys Ala Ala Ala Gly Ala
1               5                   10                  15

Ile Glu Thr Met Ala Tyr Glu Leu Gly Ala Gly Leu Gly Ile Ala
            20                  25                  30

<210> SEQ ID NO 27
<211> LENGTH: 10
<212> TYPE: PRT
<213> ORGANISM: Artificial Sequence
<220> FEATURE:
<223> OTHER INFORMATION: synthetic consensus peptide

<400> SEQUENCE: 27

Phe Gly Leu Ile Leu Thr Arg Ser Tyr Ser
1               5                   10

<210> SEQ ID NO 28
<211> LENGTH: 5
<212> TYPE: PRT
<213> ORGANISM: Artificial Sequence

```
<220> FEATURE:
<223> OTHER INFORMATION: synthetic consensus peptide

<400> SEQUENCE: 28

Ala Ser Ser Ser Ile
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic consensus peptide

<400> SEQUENCE: 29

Ala Ala Lys Thr Ala Phe Ile Ser
1               5
```